Jan. 17, 1939. J. ODER Plant Pat. 308
SNAPDRAGON
Filed June 20, 1938
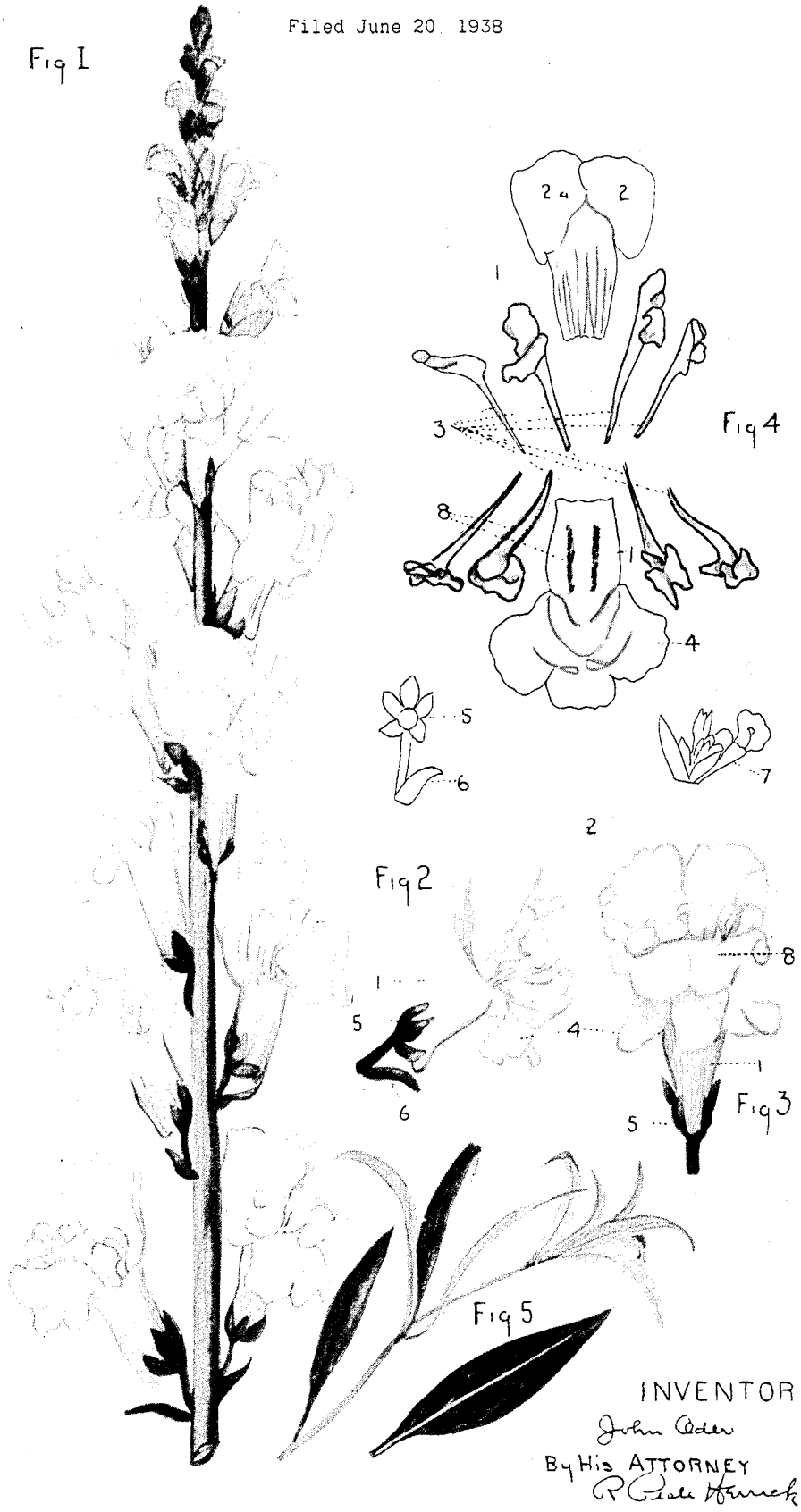
INVENTOR
John Oder
By His ATTORNEY
R Dale Hanick Patented Jan. 17, 1939

Plant Pat. 308

UNITED STATES PATENT OFFICE

308

SNAPDRAGON

John Oder, Denver, Colo., assignor to The Denver Wholesale Florists Company, Denver, Colo.

Application June 20, 1938, Serial No. 214,830

1 Claim. (Cl. 47—60)

This invention relates to plants and has special reference to a snapdragon (Antirrhinum) which I have produced.

An important object of this invention is to produce a flower of the above named type which shows a pronounced reduplication of its petal like parts.

A further object of the invention is to produce a flower of the above named variety which is very hardy and has excellent keeping qualities.

A further object is to produce a flower of the above named type that is a characteristic pink in color.

In the drawing forming a part of this application and in which like numerals are employed to designate like parts throughout the same, Fig. 1 is a perspective view embodying my invention, Fig. 2 is a side elevation of one of the blossoms, Fig. 3 is a front elevation of one of the blossoms, and Fig. 4 is a plan view of a blossom disassembled showing its respective parts, and Fig. 5 is a view of the leaves of the plant.

In the drawing embodying my invention, for the purpose of illustration, the numeral 1 designates the "corolla tube" which is formed at its upper end with oppositely disposed petal lobes 2 and 2a whose center edges overlap. The lower petal lobes 4 are three in number, somewhat crinkled on the edges and usually bearing yellow colored protuberances 8. Inside the "corolla tube" 1 are six to eight stamens 3 that have developed into narrow wrinkled petals of the same color as the remainder of the flower. These frequently bear yellow markings 8 as the petals. In very few flowers are true functional stamens present though the petals evolved from them may in frequent cases bear yellow pollen masses.

In addition to the modification of the anthers to petal-like form, the ovary, which in the usual snapdragon is a hollow organ containing numerous seeds, is replaced by a complex mass of telescoped bracts or petal-like growths designated by the numeral 7.

The plant has a sturdy stem thirty inches to six feet tall depending on the age and conditions of growth. The leaves are arranged irregularly alternate on the stem, the lower ones being larger and broader than those nearer the top. The flower head stands erect and the flowers are well spaced along the stem. At the upper end of the spike is a tip of a series of flower buds with accompanying bracts, these progressively open as the flower head ages. The flowers grow singly and at an angle between the stem and a bract 6.

The amount of flowers on each head varies from twenty-five to fifty; those at the base blooming first with a gradual blooming of those farther up on the spike. The heads may be twelve to fifteen inches long and with the proper care, the cut flowers may be kept fresh over a long period of time.

The color shown in the drawing constitutes an accurate representation of the colors of my improved original plant and its descendants, this color in the darker shades being identified as Thulite Pink and the lighter tints being Rosalane Pink according to Ridgway's "Color Standards and Color Nomenclature", Plate XXVI 71 . V–RR.

Furthermore, I do not limit myself to this color except insofar as it is recited in my claim, inasmuch as the flowers vary somewhat in this respect; also I do not limit myself to the exact shapes and appearances of the parts since the different flowers vary considerably, not only in one plant but on one single flower spike.

For the purpose of propagation cuttings of small side branches and buds may be used as the flowers rarely if ever produce seed.

Having described my invention, I claim:

A snapdragon as herein shown and described characterized by its erectness, its sturdy nature, its pink color, and a substantial reduplication of its floral parts.

JOHN ODER.